(12) United States Patent
Magana et al.

(10) Patent No.: US 9,033,917 B2
(45) Date of Patent: May 19, 2015

(54) NEEDLE CATHETER FOR DELIVERY OF AGENTS DIRECTLY INTO VESSEL WALL

(75) Inventors: Jesus Magana, Redwood City, CA (US); Paul Consigny, San Jose, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 343 days.

(21) Appl. No.: 13/586,746

(22) Filed: Aug. 15, 2012

(65) Prior Publication Data

US 2014/0052052 A1 Feb. 20, 2014

(51) Int. Cl.
*A61M 31/00* (2006.01)
*A61M 25/01* (2006.01)
*A61M 25/04* (2006.01)
*A61M 25/00* (2006.01)

(52) U.S. Cl.
CPC ..... *A61M 25/0147* (2013.01); *A61M 2025/009* (2013.01); *A61M 25/04* (2013.01)

(58) Field of Classification Search
CPC ............ A61M 25/04; A61M 25/0097; A61M 25/0147; A61M 2025/009; A61M 2025/1047; A61M 37/00; A61F 9/00745
USPC ..................... 604/22, 95.04, 96.01, 104–107, 604/528–530, 532, 535
See application file for complete search history.

(56) References Cited

U.S. PATENT DOCUMENTS

| | | | |
|---|---|---|---|
| 3,495,586 A * | 2/1970 | Regenbogen | 600/101 |
| 4,578,061 A | 3/1986 | Lemelson et al. | |
| 5,354,279 A | 10/1994 | Hoefling et al. | |
| 5,419,777 A | 5/1995 | Hoefling et al. | |
| 5,830,222 A | 11/1998 | Makower et al. | |
| 6,217,554 B1 | 4/2001 | Green | |
| 6,283,951 B1 | 9/2001 | Flaherty et al. | |
| 6,302,870 B1 | 10/2001 | Jacobsen et al. | |
| 6,302,875 B1 | 10/2001 | Makower et al. | |
| 6,375,615 B1 | 4/2002 | Flaherty et al. | |
| 6,425,887 B1 | 7/2002 | McGuckin et al. | |
| 6,458,098 B1 | 10/2002 | Kanesaka | |
| 6,558,349 B1 | 5/2003 | Kirkman | |
| 6,592,559 B1 | 7/2003 | Pakter et al. | |
| 6,629,987 B1 | 10/2003 | Gambale et al. | |
| 6,685,648 B2 | 2/2004 | Flaherty et al. | |
| 6,726,677 B1 * | 4/2004 | Flaherty et al. | 604/528 |
| 6,730,061 B1 | 5/2004 | Cuschieri et al. | |
| 6,926,692 B2 | 8/2005 | Katoh et al. | |
| 7,094,230 B2 | 8/2006 | Flaherty et al. | |
| 7,141,041 B2 | 11/2006 | Seward | |
| 7,442,184 B2 | 10/2008 | Katoh et al. | |

(Continued)

FOREIGN PATENT DOCUMENTS

WO 9526776 A1 10/1995
WO 0107113 A1 2/2001

OTHER PUBLICATIONS

International Search Report received Nov. 22, 2013.

*Primary Examiner* — Theodore Stigell
*Assistant Examiner* — Tiffany Legette
(74) *Attorney, Agent, or Firm* — Fulwider Patton LLP

(57) ABSTRACT

A system and method for treating a patient including advancing a catheter into the vasculature of the patient, forcing the catheter to adopt a position in contact with a vessel wall, and causing a needle tip to advance into the wall from a lumen in the catheter external surface that is in contact with the wall.

9 Claims, 9 Drawing Sheets

(56) References Cited

U.S. PATENT DOCUMENTS

| | | |
|---|---|---|
| 7,670,329 B2 | 3/2010 | Flaherty et al. |
| 7,842,011 B2 | 11/2010 | Maerten et al. |
| 7,922,687 B2 | 4/2011 | Gingles |
| 2005/0096590 A1* | 5/2005 | Gullickson et al. ........ 604/95.04 |
| 2005/0148929 A1* | 7/2005 | Gingles ...................... 604/95.04 |
| 2006/0167437 A1 | 7/2006 | Valencia |

* cited by examiner protoporphyrin IX
PpIX benzoporphyrin
Derivative, BPD totra (meso-hydroxy)
phenyl chlorin, mTHPC Photofrin Mono-aspartyl
chlorin e6, NPe6

Hexylpyropheo-
phorbide, HPPH

Pd-Bacterio
Pheophorbide, WST09 disulfonated (adjacent)
A1 phthalocyanine

NEEDLE CATHETER FOR DELIVERY OF AGENTS DIRECTLY INTO VESSEL WALL

BACKGROUND

The present invention relates generally to medical devices, systems, and methods for treating disease. More particularly, the invention relates to a system and method for achieving neuromodulation via an intravascular-delivered compound or drug.

Hypertension, or high blood pressure, affects a large proportion of the world's adult population. Renal, or renovascular, hypertension can be caused by hypoperfusion of the kidneys due to a narrowing of the renal arteries. The kidneys respond by giving off hormones that signal the body to retain salt and water, causing the blood pressure to rise. The renal arteries may narrow due to arterial injury or atherosclerosis. Despite effective drug regimens to regulate the renin-angiotensin-aldosterone pathway or to remove excess fluid from the body and reduce blood pressure, many patients with hypertension suffer from resistant forms of the disease.

Resistant hypertension is a common clinical problem, caused when a patient is unable to control high blood pressure by medication alone. Resistant hypertension is especially a problem in old and obese people. Both of these demographics are growing. While symptoms are not obvious in these patients, cardiovascular risk is greatly increased when they are unable to control their blood pressure.

The sympathetic nervous system (SNS) operates through a series of interconnected neurons that are part of both the peripheral and central nervous system. Through chemical synapses, the sympathetic nervous system is able to release chemical messengers that produce chemical chain reactions, which ultimately elicit physiologic responses. Therefore, messages traveling through the sympathetic nervous system can trigger changes in many bodily functions, including the up- and down-regulation of vascular tone (vasoconstriction and vasodilation, respectively). Vasoconstriction can be triggered by the release of Angiotensin I and its conversion into Angiotensin II. Angiotensin II directly causes the constriction of blood vessels, which then increases the systemic blood pressure. In certain situations, this increase in systemic blood pressure manifests itself in hypertension that can have a detrimental effect on numerous processes, including inhibiting blood flow to the kidneys, promotion of atherosclerosis, and stimulation of hypertrophy.

Hypertension is also caused by hyperactive renal sympathetic nerves. Renal sympathetic efferent and afferent nerves run generally longitudinally along the outside of arteries leading from the aorta to the kidneys. These nerves are critically important in the initiation and maintenance of systemic hypertension. It has been shown that by severing these nerves, blood pressure can be reduced.

Noting the strong correlation that exists between sympathetic nervous system function and many life threatening diseases, a strong suggestion exists that a potential therapy would be to control the activity of the sympathetic nervous system. Indeed, research has shown that stimulation of afferent nerves can have a profound affect on sympathetic activity and related blood pressure. Aars, et al., *Reflex Changes in Sympathetic Activity and Arterial Blood Pressure Evoked by Afferent Stimulation of the Renal Nerve* (1970). Furthermore, patent publications have disclosed catheter devices intended to ablate sympathetic nerves that otherwise innervate cardiac tissue, and furthermore that such ablation beneficially treats cardiac fibrillation, tachycardia, or cardiac arrhythmia. See for example U.S. Pat. No. 6,292,695 (issued 2001).

Percutaneous or endoscopic interventional procedures are very common in the United States and other countries around the world. Intravascular catheter systems are used for procedures such as balloon angioplasty, stent placement, atherectomy, retrieval of blood clots, photodynamic therapy, and drug delivery. All of these procedures involve the placement of catheters into arteries, veins, or other lumens of the body in order to provide access to the deep recesses of the body without the necessity of open surgery.

In cases where renal arterial occlusion is causing hypertension that cannot be controlled with medication, another potential therapy includes balloon angioplasty of the renal artery. In rare cases, surgical bypass grafting may be considered as a therapeutic alternative. While renal angioplasty can be effective in reducing blood pressure, angioplasty is plagued with resulting restenosis due to elastic recoil, dissection, and neointimal hyperplasia. Renal stents may improve the result, but also lead to restenosis or renarrowing of the artery due to neointimal hyperplasia.

While renal denervation had been performed with surgical methods in the past, more recently a catheter-based therapy to heat and destroy the nerves from within the renal artery using radio-frequency ablation has been studied.

While the use of catheter-based radiofrequency (RF) denervation appears to have a therapeutic effect, it is unknown what long-term implications will arise from the permanent damage caused to the vessel wall and nerves by the RF procedure. Radiofrequency energy denervates the vessel by creating heat in the vessel wall. The RF probe contacts the inner lining of the artery and the RF energy is transmitted through the tissue.

However, nerve ablation by catheter to disrupt sympathetic nervous system activity has its drawbacks. For example, ablation of the nerve bundles may be inconsistent or incomplete. Also, although catheterization is considered minimally invasive, it would be preferable to achieve therapy through non-invasive methods, such as through extracorporeal means. Furthermore, access to particular areas of the sympathetic nervous system may be difficult or impossible to achieve through catheterization, given that the sympathetic nervous system also exists outside of vascular walls in areas that a catheter cannot reach.

For all of these reasons, it would be desirable to provide additional and improved systems and methods for delivery into the adventitial/perivascular/periarterial space of the renal arteries, sympatholytic or sympathetic nerve blocking agents, including other agents that can modulate nerve function, to accomplish biological and reversible denervation while not creating injury to the blood vessel or aggravating the underlying vascular disease. As a result, there is a need for a means of disrupting sympathetic nervous system afferent and efferent activity in a non-invasive manner that allows any location of the sympathetic nervous system to be targeted for therapy.

In a further aspect of the prior art, systems are known for injecting drugs and agents into a patient from deep within the vascular anatomy of the patient. Typically, these systems will locate the catheter at a fixed position within the radial center of a vessel using inflatable or expandable means, and a needle will be advanced to protrude from the catheter and penetrate the tissue of the vascular wall. A problem with such prior art systems is that a physician typically has difficulty determining how deep into the tissue the needle has advanced. This problem arises because the needle must first advance radially a certain distance from the catheter and through the space in the vessel before it reaches the vessel wall. Depending on the local anatomy of the vessel, this distance is not predictable, and cannot be seen with adequate precision using fluoroscopic methods. Thus, even if a physician knows exactly how far the needle tip has extended from an external wall of the catheter, she cannot assess how far the tip has penetrated into tissue because the distance between the catheter and the vessel wall is unknown.

As a result, there is a need in the art for an injection catheter that may be used to insert a needle into the vascular wall by a distance that it precisely known by the physician. This invention addresses these and other needs.

SUMMARY OF THE INVENTION

The present invention is a system for intravascular treatment. It comprises a catheter having an elongate axis defining a lumen configured for receiving a hypotube. The lumen terminates at a distal opening in an external side wall of the catheter. A hypotube is slidably received within the lumen, the hypotube having a sharpened distal tip and being configured in relation to the catheter to have a retracted condition in which the distal tip is contained entirely within the lumen, and an advanced condition in which the distal tip protrudes from the distal opening.

A plurality of positioning wires extend external to the catheter, the wires being configured in relation to the catheter to have an unexpanded condition for intravascular delivery in which each wire is collapsed against the an external wall of the catheter, and an expanded condition for positioning the catheter within a vessel in which each wire is flexed away from the catheter along an imaginary plane extending radially away from the elongate axis. Under this configuration, all imaginary radial planes occupied by a flexed wire are included within an angular arc about the elongate catheter axis of not more than 180 degrees. Preferably, the flexed wires in the expanded condition are located in relation to the catheter so that the angular arc has a center that is substantially diametrically opposite the position of the distal opening. Under this configuration, causing the positioning wires to assume an expanded condition causes the wires to press against one side of the vessel wall and thus to force the catheter against a diametrically opposite wall of the vessel so that the distal opening is in direct contact with the vessel wall. Thus, when the sharpened tip of the hypotube is caused to extend from the distal opening, it is compelled to penetrate directly through the vessel wall into perivascular space, without having to cover any distance between the catheter and the vessel wall.

The system further includes a means for placing each positioning wire under a compressive axial force, whereby each wire is flexed away from the catheter in the expanded condition. In some embodiments, the means for placing each positioning wire under a compressive axial force includes a rack and pinion, wherein the rack is configured to move a proximal end of each wire in a distal direction. In other embodiments, the means for placing each positioning wire under a compressive axial force includes a pull element to which a distal end of each wire is attached, the pull element being configured for proximal movement in relation the catheter. The pull element may be slidably received within a lumen of the catheter, and the distal end of each positioning wire may be connected to the pull element whereby proximal movement of the pull element causes the wires to flex and assume the expanded condition. In some embodiments, the pull element may define a lumen for receiving a guidewire.

The system further includes a means for moving the hypotube from the retracted condition distally to the advanced condition. In some embodiments, the means for moving the hypotube from the retracted condition distally to the advanced condition includes a rack and pinion. In one embodiment, the plurality of positioning wires are four in number. In yet further embodiments, the system may include a plurality of positioning lumens extending through the catheter, wherein each wire extends through a positioning lumen for at least a portion of the length of the wire, and wherein the wires extend external to the catheter for a first length, and the distal opening is located at a position that is substantially midway along the first length. Under this configuration, the force applied to the catheter by the positioning wires is centered on the distal opening, so that the distal tip of the hypotube may be allowed to penetrate the vessel wall where the catheter is forced snugly against the vessel wall, and the user may be confident that the entire length of the hypotube that emerges from the catheter will penetrate through the vessel wall into perivascular space.

In another embodiment, the invention is a method of treating a patient for a medical condition. The method comprises advancing a catheter having an elongate axis into a vessel of the patient. A force is applied on the catheter that is directed perpendicular to the axis, thereby forcing an external side wall of the catheter into contact with a wall of the vessel. A hypotube having a sharpened distal tip is advanced through an opening of a lumen in the catheter, thereby penetrating the vessel wall with the sharpened tip at a location where the external side wall of the catheter is in contact with the vessel wall. Once this force has been applied, an agent is injected through the hypotube and through the vessel wall into perivascular space. Under this configuration, a user may be confident that sharpened tip of the hypotube will penetrate through the vessel wall at a location where the catheter is in contact with the vessel wall, and therefore that all of the length of the hypotube that extends from the catheter will extend into perivascular space surrounding the vessel. Thus, the user may be confident in knowing the complete extent of penetration by the hypotube. In some embodiments, applying a force on the catheter includes applying an axially compressive force to a plurality of wires extending along an exterior portion of the catheter, thus to cause the wires to buckle and bend radially away from the catheter. In other embodiments, applying an axially compressive force to a plurality of wires includes moving a proximal end of the wires towards a distal end of the catheter, and in yet other embodiments, applying an axially compressive force to a plurality of wires includes moving a distal end of the wires towards a proximal end of the catheter.

These, and other advantages of the invention, will be more fully understood when read in light of the figures and the brief description of the preferred embodiments.

DETAILED DESCRIPTION OF THE PREFERRED EMBODIMENTS

Figure 1:
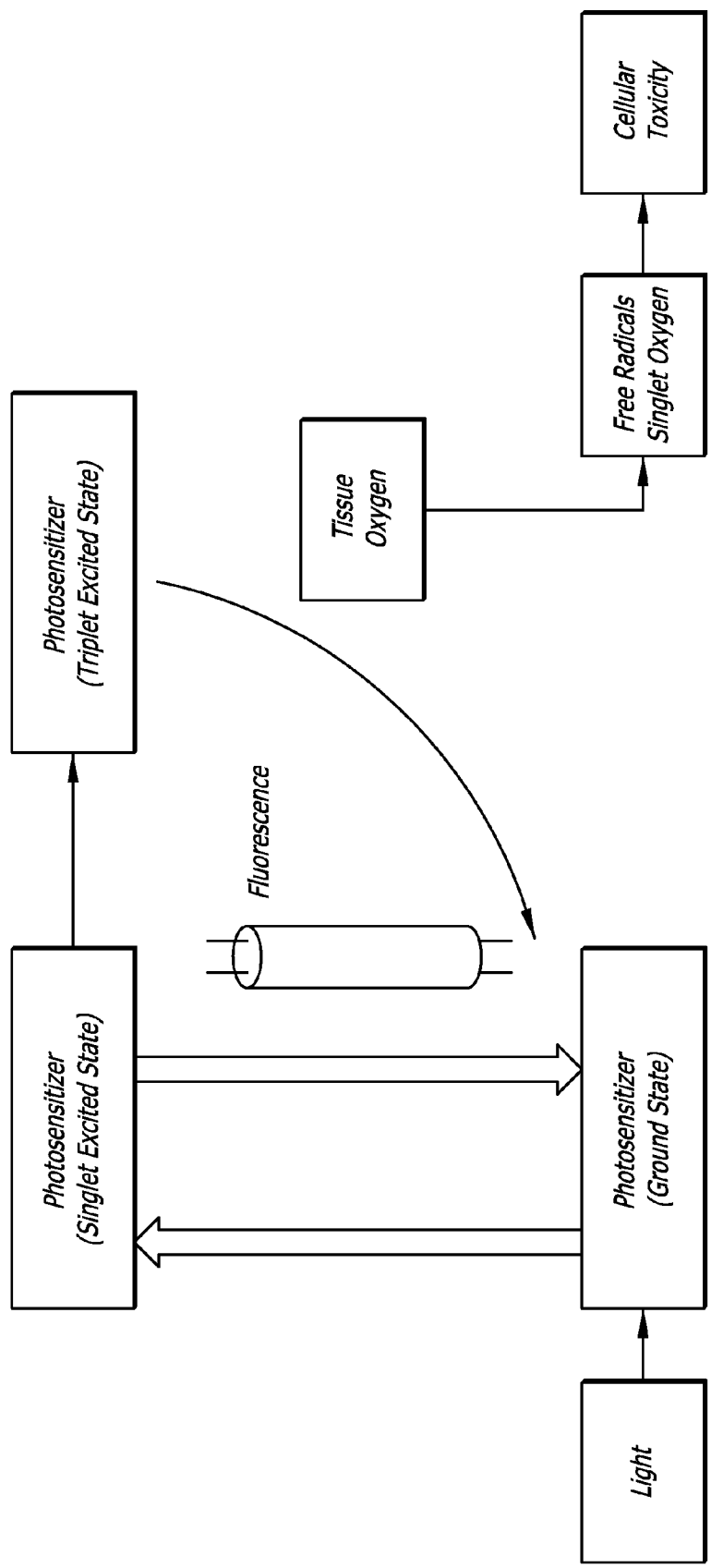
FIG. 1 is a schematic drawing of a process that may be used in some embodiments of the invention.

The present application discloses embodiments of the invention, in which systems and methods are described for introducing materials to the sympathetic nervous system surrounding the renal arteries of a patient. In some embodiments, the materials are capable of generating localized singlet oxygen that in turn are cytotoxic to the sympathetic nervous system, and are delivered in order to denervate or modulate the nervous system surrounding the renal arteries.

The components of some embodiments of the system may include:

(a) a photosensitizing agent, in the form of a solution in a solvent matrix or alternatively in a form of nano- or microparticles in bio- or non-biodegradable polymers;

(b) an injection catheter configured to inject the sensitizer or particulate formulation into the periarterial/preadventitial space of the renal arteries in a patient; and (c) a light catheter capable of generating light at the same wavelength that would be absorbed by the sensitizer, and further capable of being inserted into the renal arteries of a patient.

In an application of the system and methods of the invention, some embodiments include injecting a photosensitizer agent into a desired location surrounding the renal arteries of the patient, followed by applying light energy from the catheter that penetrates through the wall of the artery to reach the injected photosensitizer, whereupon neurotoxic effects of the sensitizer are activated and have the effect of ablating or modulating the nerves surrounding the renal arteries. Turning now to a more detailed description of components and method of the invention:

Photodynamic Therapy is a method that involves the interaction between three components: a photosensitive agent, light, and tissue oxygen. Photosensitive agents include porphyrins or chemicals of similar structure. They can be introduced either topically or systemically. At therapeutic concentrations, most photosensitizers have no discernable effects in isolation, but they require the local application of light at a wavelength that matches the absorption characteristics of the sensitizer. The timing of light delivery following the delivery of a sensitizer is crucial for achieving the desired biological response, and varies with the pharmacokinetics of individual sensitizers.

In order to advance this result, light—usually in the form of red light from a laser—is delivered at a power level that avoids the thermal effects that were a feature of early laser angioplasty. When subjected to light applied at the appropriate power level and wavelength, the photosensitizer is transformed into an electronically excited state that can transfer its energy either to tissue oxygen to generate singlet oxygen, or to other biomolecules to yield other free radical intermediates. The short half-life ($0.6 \times 10^{-6}$ s) and diffusion distance (0.1 µm) of singlet oxygen and other active species means that cellular effects are highly localized to the site where these species are produced. The activation of photosensitizers that have been incorporated into cell membranes results in swelling, bleb formation, and shedding of vesicles, as well as in the inhibition of membrane transport systems such as Na+/K+-ATPase. Other sites affected include mitochondria, the Golgi apparatus, the rough endoplasmic reticulum, and lysosomes. Cytotoxicity is mediated at a cellular and subcellular level and may occur by apoptosis or necrosis.

These actions are schematically shown in FIG. 1, where a mechanism of action of photodynamic therapy is exemplified. Photosensitizing agents are activated by light of a specific wavelength. In its excited state the photosensitizer reacts with tissue oxygen to yield various reactive oxidative species, inducing specific cellular and extracellular effects that lead to cellular and tissue damage.

Figure 2:
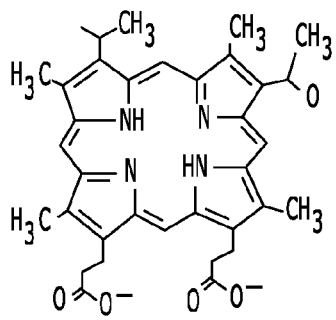
FIG. 2 is a schematic drawings of chemical compounds that may be used in embodiments of the invention.
Figure 2:
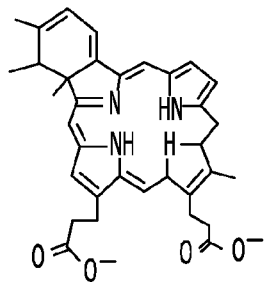
Figure 2:
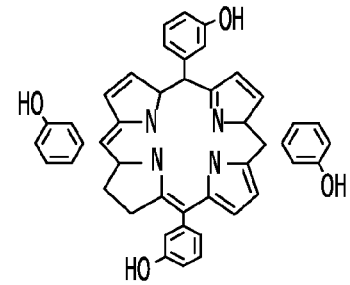
Figure 2:
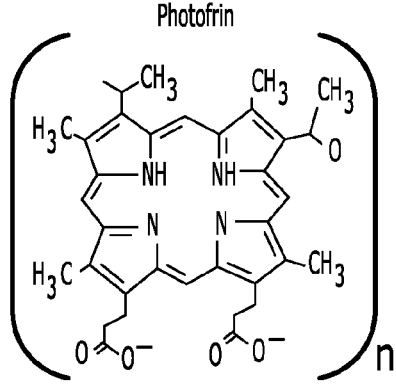
Figure 2:
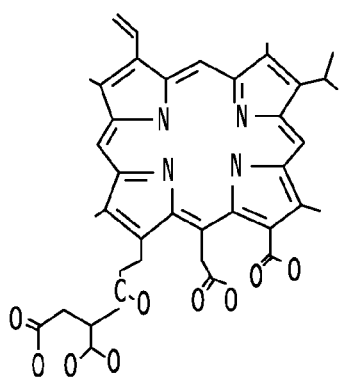
Figure 2:
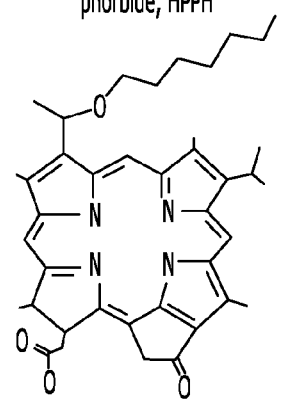
Figure 2:
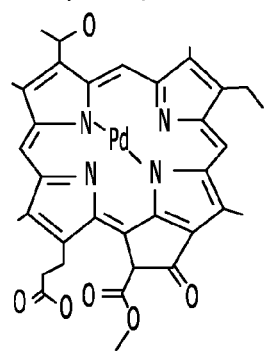
Figure 2:
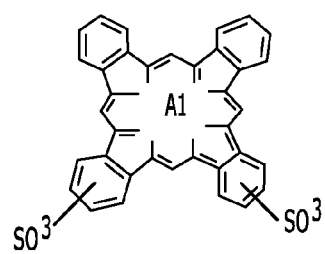

The laser wavelength used in embodiments of the invention is preferably selected to be long enough to penetrate the arterial tissues from the light source positioned within an artery. Generally, increasing the laser wavelength increases the depth of penetration of the laser into the tissues. The laser emitting wavelength is preferably configured to be in the range of 400-900 nm. More preferably, the wavelength is in the range of 500-800 nm since there are many photosensitizers for which the quantum yield (i.e., the yield that a photon of light energy converts triplet oxygen into singlet oxygen) is relatively high. The photosensizer used in embodiments of the invention is preferably selected from one, or more, of the following a. hematoporphyrin derivative (HPD)
b. porphyrins
c. benzoporphyrin derivative monoacid ring A (BPD-MA)
d. phthalocyanines and naphtalocyanines
e. texaphyrins
f. cationic fullerenes
g. 2-[1-hexyloxyethyl]-2-devinyl-pyropheophrbide-a (HPPH)
h. chlorins and bactenochlorines FIG. 2 exemplifies these and other chemical structures and properties of some clinically known photosensitizers. It should be mentioned that hydrophobic and amphiphilic phototosensitzers are generally more efficient in sensitizing cells to photoinactivations due to the longer lifetime of singlet oxygen in hydrophobic environments, and easier penetration of such photosensitizers through and into membranes. It should also be mentioned that many photosensitizers may exist as many ionic species in biological environments, and some of these may be hydrophobic.

An injection catheter suitable for use as a component in some embodiments of the system and method of the invention is here described. Such a catheter is configured in size and flexibility to be inserted by minimally invasive means until the distal end of the catheter resides in the renal artery of a patient. The distal end of such a catheter is equipped with an injection needle that may have two conditions: a first condition in which the needle is slidingly retracted into a lumen within the catheter, a condition which permits the catheter to be introduced into and through the renal artery without interference from the needle; and, a second condition in which the needle may be extended from the catheter to penetrate the wall of the renal artery, from which position a suitable photosensitizing agent may be injected via the needle into the space surrounding the renal artery.

Figure 3:
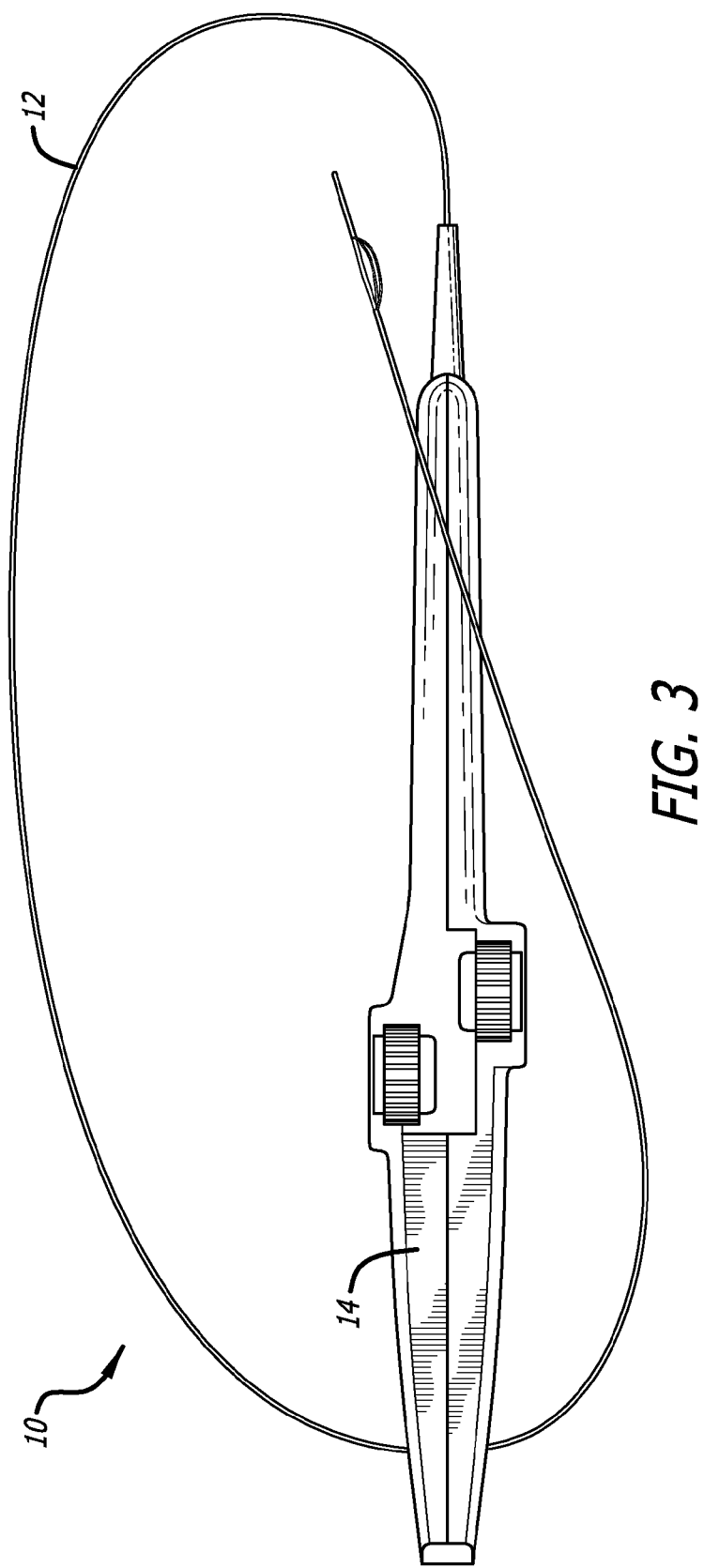
FIG. 3 is a perspective view of an embodiment of a catheter system that may be used in the invention.
Figure 4:
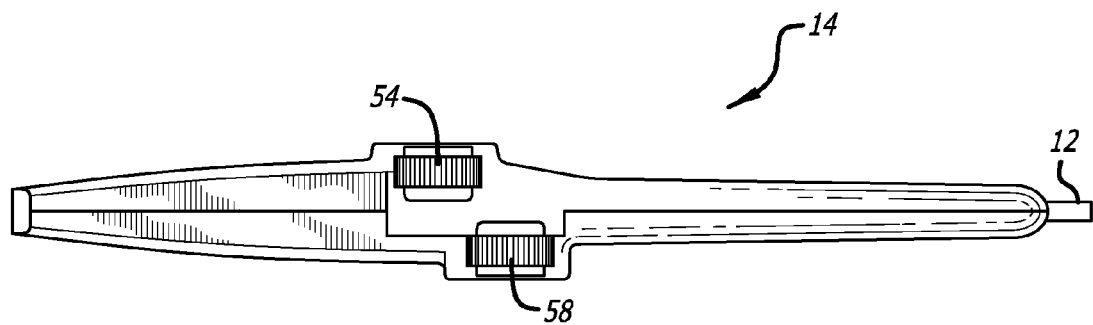
FIG. 4 is a perspective view of a handle that may be used in the system shown in FIG. 3.
Figure 5:
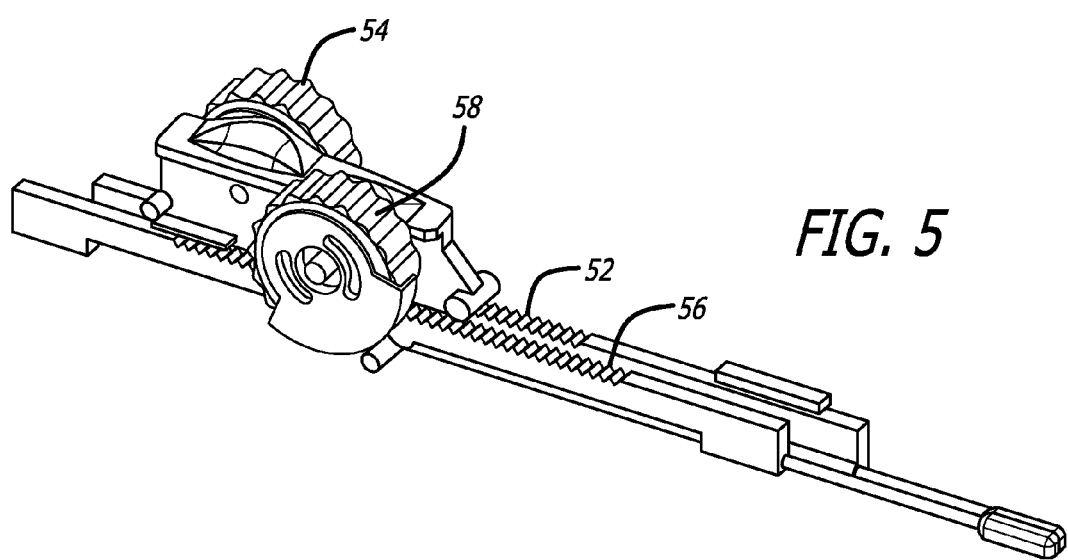
FIG. 5 is a perspective view of components of the handle show in FIG. 4.

With reference to FIGS. 3-12, some embodiments of the system and method are described. A general view of an embodiment of an entire catheter system is seen in FIG. 3, generally indicated by the numeral 10. The system 10 includes a distally positioned flexible catheter 12 which is operable by a proximally positioned handle 14.

The catheter 12 is configured in size and flexibility to be insertable by minimally invasive means into the vasculature of a patient so that the distal portion thereof is locatable within a vessel of the patient, preferably a renal artery. The catheter 12 of a first embodiment includes a plurality of lumens disposed axially within the catheter to enable functions that will now be described. A first lumen 16 is provided that is sized to receive a guidewire 17 of known configuration so that the catheter is threadable over the guidewire previously introduced into the vasculature. (Guidewire 17 shown in FIGS. 9, 10—but, for clarity, not shown in FIGS. 6, 7, 8, 11, and 12) In some embodiments, the catheter may be configured as an over-the-wire (OTW) type guidewire, but it may also be configured as a rapid exchange type guidewire.

The catheter 12 includes a second lumen 18 that is sized to receive a sharpened hypotube 20 having an internal lumen 21. The second lumen extends from the proximal to the distal portions of the catheter 12. The hypotube is configured to function as a hypodermic needle, with a sharpened distal tip 22. In a retracted condition, the tip of the needle is withdrawn along the second lumen 18 into the body of the catheter 12 to facilitate advancement of the catheter through the vasculature of the patient. Once the catheter 12 has reached a desired position in the vasculature, the hypotube may be advanced a few millimeters along the lumen 18 (by advancement means within the handle 14 as described below) to extend a precise distance "D" from an opening 24 on the outer surface of the catheter, as seen for example in FIGS. 7, 9, 11, and 12. In this extended condition, the needle tip is configured to penetrate the wall of the vessel to precisely position the needle tip at a desired location within the tissue of the periarterial space (identified as "P.V." in FIG. 7) surrounding the artery (identified as "V" in FIG. 7).

In addition to the first and second lumens 16, 18 a further set of lumens is included to extend along the length of the catheter 12. In some embodiments the further set of lumens has between three and five lumens in number, and most preferably four in number, identified in the figures by the numerals 26a, 26b, 26c, and 26d (or collectively, 26).

Figure 6:
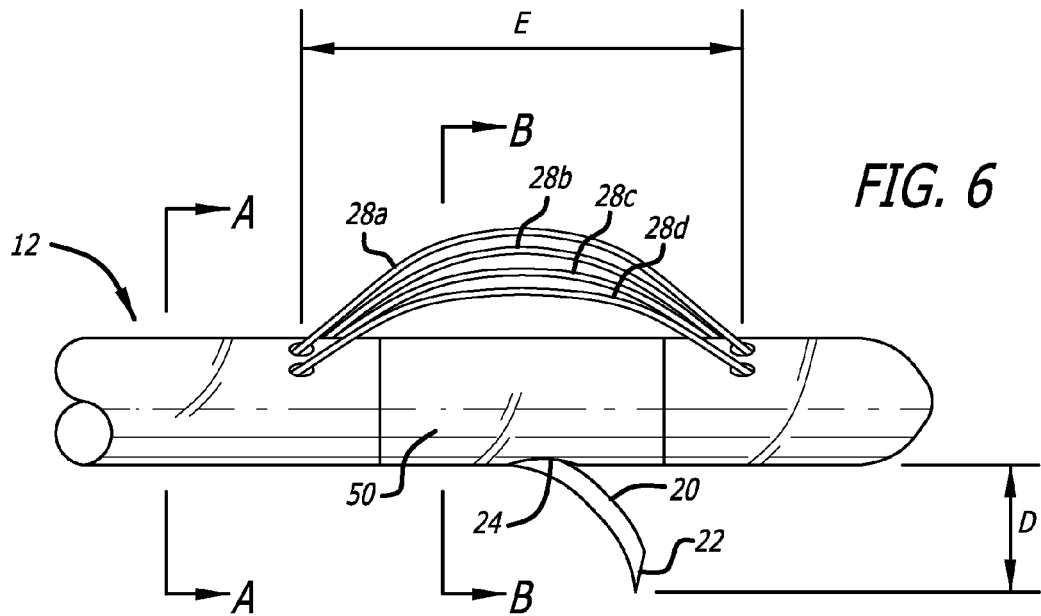
FIG. 6 is a side elevational view of one embodiment of a distal component of a catheter having features of the invention, shown in an expanded condition.
Figure 7:
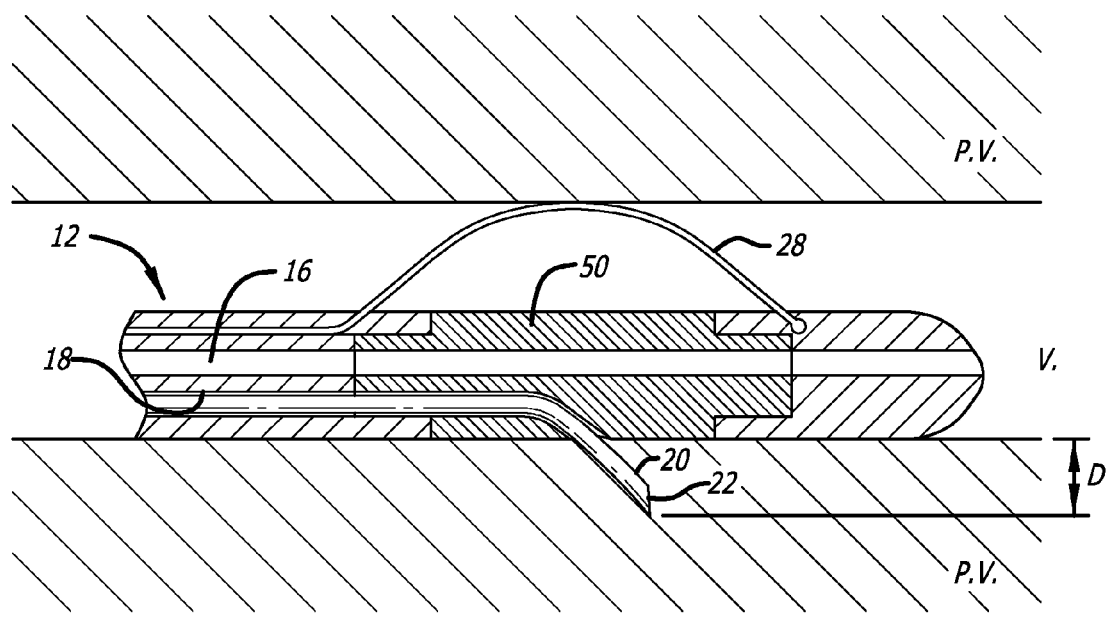
FIG. 7 is a sectional view of the embodiment shown in FIG. 6 within vascular environment shown in the background.
Figure 8:
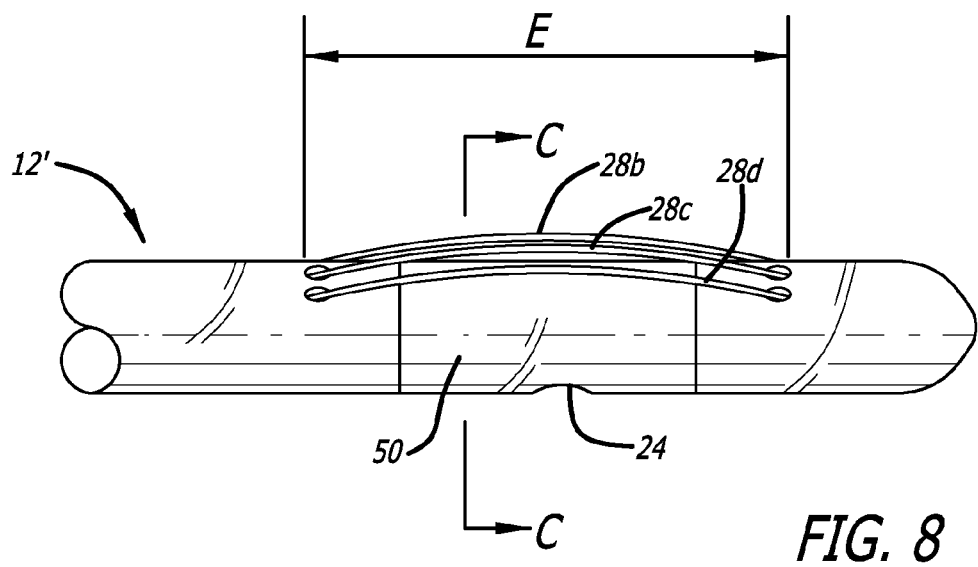
FIG. 8 is a side elevational view of the embodiment of FIG. 6, shown in a collapsed condition.
Figure 10:
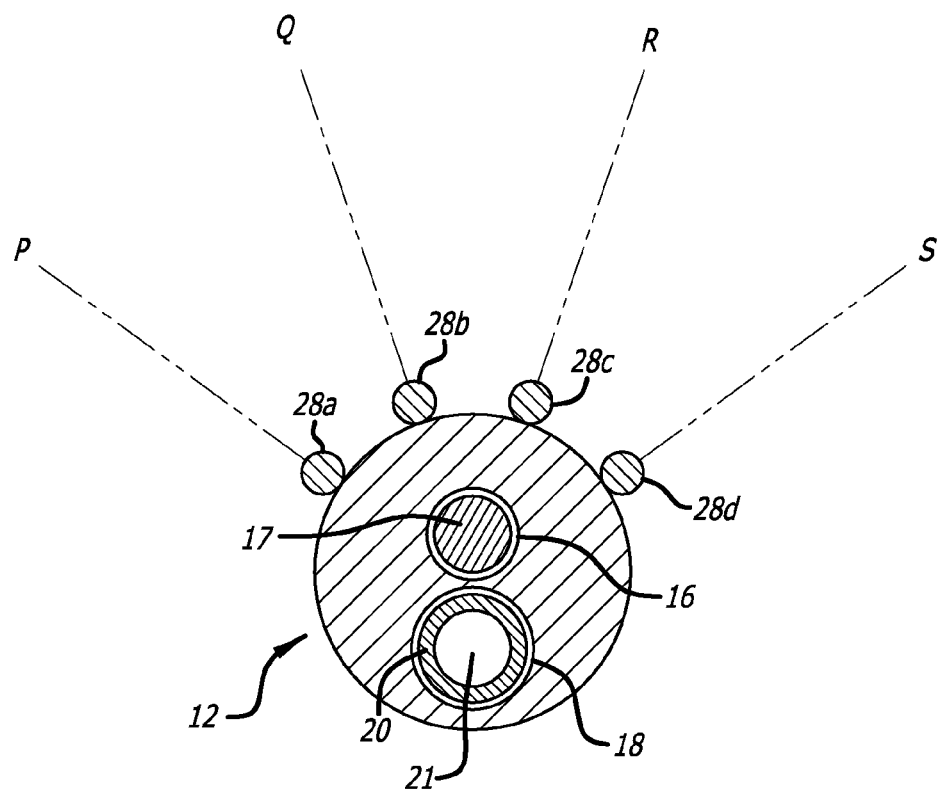
FIG. 10 is a sectional view of the embodiment shown in collapsed condition of FIG. 8, taken substantially along the line C-C.
Figure 9:
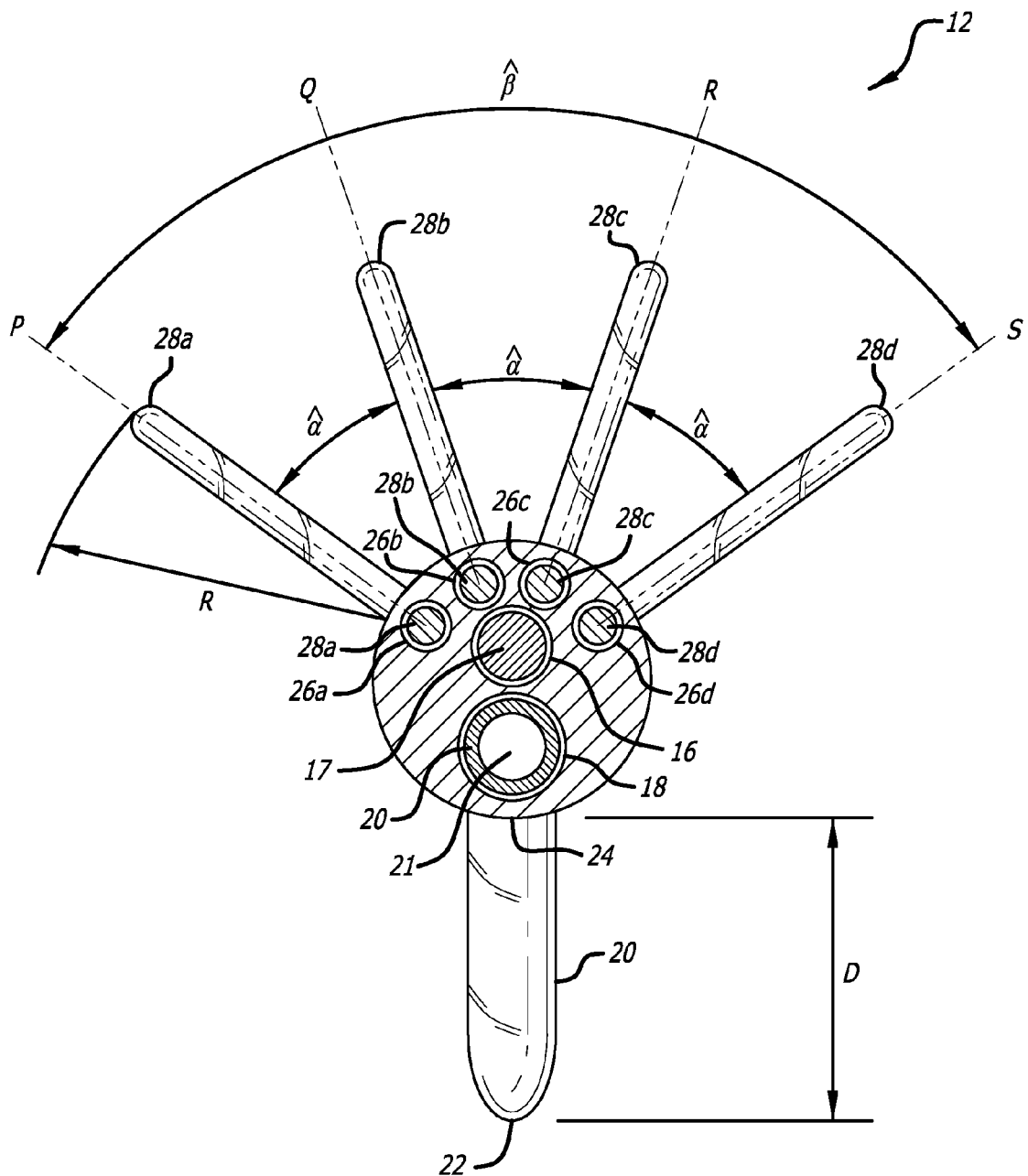
FIG. 9 is a sectional view of the embodiment of FIG. 6, taken substantially along the line A-A.

Extending along the length of each positioning lumen is a positioning wire with corresponding identification numerals 28a, 28b, 28c, 28d (or collectively, 28). Each positioning wire is preferably made of a shape memory alloy, such as nickel titanium alloy, and is configured to emerge from its associated lumen near the distal end of the catheter and to extend along the exterior of the catheter for a short distance "E" (as indicated in FIGS. 6, 8) before the distal tip of each wire is fixedly attached to the body of the catheter. The length "E" and position of each positioning wire that extends along the outside of the catheter is configured so that the needle opening 24 in the catheter is positioned at about the midpoint of this length. Under this configuration, when a compressive axial force is applied to each of the positioning wires 28, the wires buckle in the region where they are positioned outside the catheter, and extend radially away from the catheter as shown in FIGS. 6, 7, and 9. In this embodiment, the catheter 12 is configured such that a compressive axial force is applied to the positioning wires by pushing a proximal end of the positioning wires towards their distal end as set forth more fully below.

In some embodiments, the positioning wires may be configured in relation to the catheter 12 so that the portion of each positioning wire that extends outside the positioning lumen (over the distance E) is caused to flex radially away from the elongate catheter along an imaginary plane (identified in FIG. 9 as radially extending planes P, Q, R, and S that are seen "end-on," and that extend along the catheter axis and substantially radially away from the axis. Under this embodiment, all the positioning wires are configured in relation to the catheter such that, when flexed away from the catheter, all imaginary radial planes occupied by a positioning wire are included within an angular arc (identified as the angle β in FIG. 9) about the elongate axis of not more than 180 degrees, and preferably not more than 120 degrees. Preferably, the angles within the arc separating one wire from an adjacent wire (identified as the angles α in FIG. 9) are all equal so that the wires are spread out evenly within the arc. Further, the flexed positioning wires may be located in relation to the catheter so that the center of the angular arc is substantially diametrically opposite the position of the distal opening 24 as exemplified in FIG. 9. And yet further preferably, the center of the distance over which the positioning wires extend external to the catheter (the distance E) is configured to substantially coincide, in the axial direction of the catheter, with the opening 24, as may be seen in FIG. 6. This configuration may be utilized to allow a physician, by merely causing the positioning wires to expand, to position the needle orifice 24 in direct contact with the vessel wall before deploying the needle 20.

Figure 11:
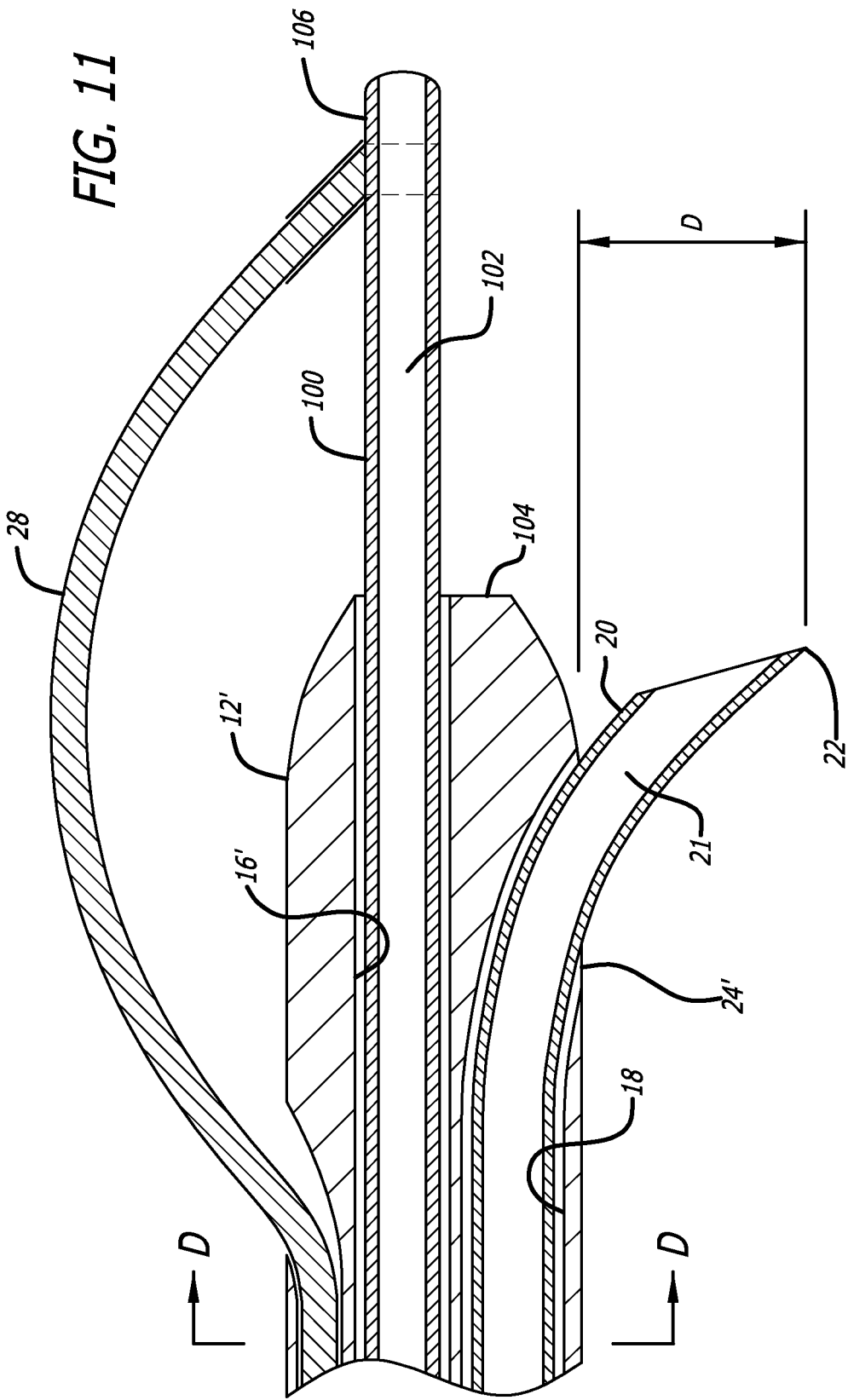
FIG. 11 is sectional view of a further embodiment of a distal component of a catheter having features of the invention, shown in an expanded condition.
Figure 12:
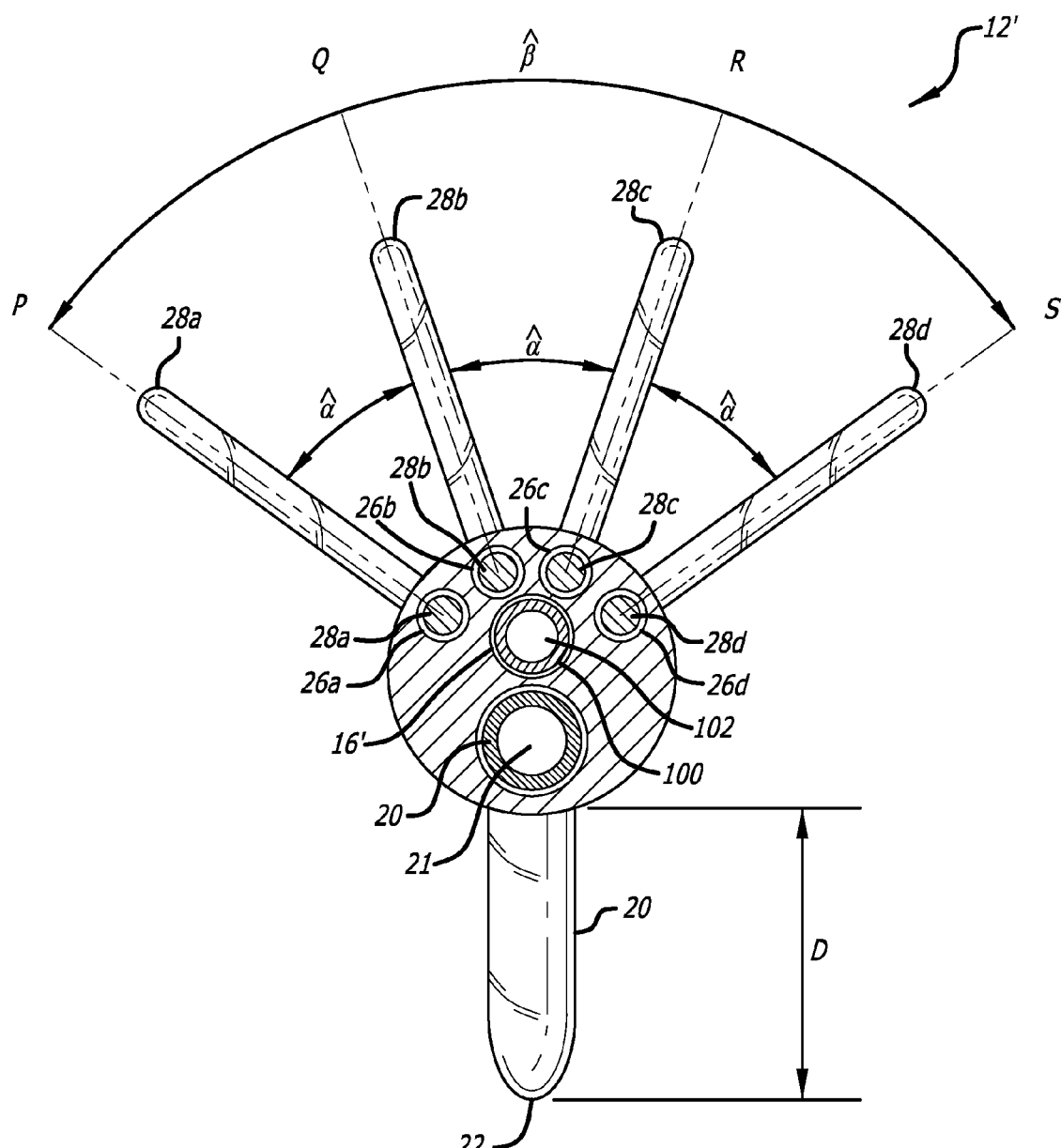
FIG. 12 is a sectional view of the embodiment of FIG. 11, taken substantially along the line D-D.

Another embodiment exemplified in FIGS. 11 and 12, a catheter 12' is described. In this embodiment, the positioning wires 28a, 28b, 28c, 28d are configured to be placed under compression by pulling their distal ends proximally while holding the proximal ends stationary. In this embodiment of the catheter 12', a lumen 16' is provided that has a diameter configured to slidably receive a pull element 100 extending from the proximal end to the distal tip 104 of the catheter. The pull element defines an internal lumen 102 configured to receive a guidewire (not shown in FIGS. 11, and 12)). The pull element extends beyond the distal tip of the catheter, and the distal ends of the positioning wires are connected adjacent the distal tip 106 of the pull element 100 by suitable means such as soldering. Under this configuration, the catheter has two conditions. In a first condition (not shown in the figures) the pull element 100 is extended distally until the positioning elements lie flat against the catheter 12', thereby diminishing the profile and enabling the catheter to be inserted into a vascular passageway. In a second condition, exemplified in FIGS. 11 and 12, the pull element 100 is retracted proximally. This action causes the positioning wires 28a, 28b, 28c, 28d to buckle and flair radially outwardly away from the catheter axis, as previously described above, with the resulting advantages. It will be appreciated that, in this embodiment, it is not essential for the positioning wires to extend all the way back to the proximal end of the catheter. Rather, they may be fixedly attached to the catheter a short axial distance behind the opening 24'.

In some embodiments, the catheter may include a translucent portion 50 inserted into the length of the catheter. (FIGS. 6 and 7.) The translucent portion 50 may be located along the length of the catheter so as to include the needle opening 24. The translucent portion is made of optically clear, or substantially clear, material such as translucent acrylic. As will be described below, the catheter is configured to allow either the guidewire or the hypotube to be withdrawn from its lumen, and allowing a fiber optic cable (not shown in the figures) to be inserted into the vacant lumen all the way up to the translucent portion 50. The length of the fiber optic cable may be configured so that, once the distal tip of the cable reaches the translucent portion of the catheter, the cable has reached the full length of its travel in the catheter and can travel no further. At this stage the translucent portion 50 and the tip of the cable are in registration and are ready for use. A source of light energy (in some embodiments, laser) may then be applied to the proximal end of the fiber optic cable, thereby to travel by known principles of total internal reflection all the way to the distal tip were it may emerge from the cable under the action of a light diffusion reflector. The light diffusion reflector may be configured to focus the light into the region of the vascular wall adjacent the needle opening 24, or it may be configured to focus the light in a circumferential path around the vessel wall. The use of these elements will be described further below.

The handle assembly 14 at the proximal end of the injection system is configured for connecting to fluid sources (for flowing agent, and/or flushing fluid in the catheter lumens), and provides access to the first lumen 16 and the second lumen 18.

The handle 14 also includes a positioning means configured to cause the positioning wires 28a, 28b, 28c, 28d to be placed under an axially compressive load when it is desired to cause the positioning wires to bend away from the catheter for fixing the distal end of the catheter at a desired location within a vessel. The positioning means includes a first rack 52 and pinion 54 combination. The first pinion is exposed sufficiently from the handle profile to allow a user to rotate the pinion with her thumb, thereby to extend the rack 52 distally.

In one embodiment, the positioning wires are operably connected to the rack, so that forward rotation of the first pinion causes the positioning wires to extend distally thereby placing them under an axially compressive load, and to flare outwardly by buckling at the distal end of the catheter, suitable for forcing the catheter against the vessel wall. Retraction rotation causes the positioning wires to revert to their collapsed condition adjacent the catheter, suitable for withdrawal of the catheter.

In another embodiment, exemplified in FIGS. 11 and 12, the pull element 100 may be operably connected to the rack, so that rearward rotation of the first pinion 54 causes the pull element to extend proximally, thereby placing the positioning wires under an axially compressive load, and thus causing them to flare outwardly by buckling at the distal end of the catheter, suitable for forcing the catheter against the vessel wall. Forward rotation causes the positioning wires to revert to their collapsed condition adjacent the catheter, suitable for withdrawal of the catheter.

The handle assembly 14 further includes a vessel wall penetration means configured to advance the needle hypotube 20 once the catheter has been positioned at a desired location within the vessel. The vessel wall penetration means includes a second rack 56 and pinion 58 combination that also operates by rotation by the user's thumb. In this case, the rack 56 is operably connected to the hypotube 20, and forward rotation causes the hypotube to advance distally, and return rotation causes it to withdraw proximally.

As seen in the figures, the two pinion gears 54, 58 are positioned adjacent each other, slightly separated in the axial direction, to provide the user with ease of movement and flexibility.

In use, the catheter system may be applied as follows in some embodiments. First a guidewire may be threaded by known method to the desired location of the vasculature of a patient. The catheter 12 is then threaded over the guidewire percutaneously in a low profile configuration (GIS. 8, 10) in which the distal tip 22 of the needle 20 is retracted into the catheter and the positioning wires 28 are in a collapsed state, until the tip of the catheter reaches the desired position within the patient's vessel. Locating the position of the catheter may be achieved by known fluoroscopic methods. Preferably, the needle opening 24 may be marked out with radiopaque markers (not shown), so that the position of the needle opening within the artery may be observed by the physician. When the needle opening 24 is positioned precisely at the desired location within the vasculature, the first pinion 54 may be rotated forward to advance the positioning wires within the catheter. This action causes the positioning wires to flare radially away from the catheter, as seen in FIGS. 6, 7, and 9, and thereby to force the catheter portion defining the needle opening 24 directly onto the wall of the renal artery. The first pinion may be locked in position by known means to temporarily restrain the pinion from rotating and thus to restrain the positioning wires from losing their flared configuration. In the alternative embodiments of FIGS. 11 and 12, the user may rotate the pinion rearwardly to retract the pull element 100, and thereby to cause the positioning wires 28 to buckle and flare outwardly, with a similar result as in the previous embodiment. A similar locking means may also be used here for the same purpose. Thus, the extent of the flared configuration may be selected and locked into place to suit the size of the vessel.

At this point, the user may forwardly rotate the second pinion 58, thereby advancing the needle 20 distally along the lumen 18. The second pinion 58 may have markings to indicate exactly how deep the needle tip has been extended from the catheter, and hence how far the needle tip has been advanced into the periarterial/perivascular space "P.V." (FIG. 7).

One advantage provided by the catheter configuration is that, because the lumen opening 24 is in direct contact with the vessel wall, as exemplified in FIG. 7, it allows the physician to know the precise depth "D" the needle must have penetrated into the vessel tissue. Thus, all movement of the needle takes place within the vessel tissue. This aspect overcomes features of the prior art in which the needle starts to move from a position in the radial center of the vessel of which the dimensions are not precisely known by the physician. Accordingly, although a physician using such prior art injection devices may know how far the needle tip has travelled outside of the catheter, a user does not necessarily know how far the needle tip has advanced into the wall of the vessel because the needle tip must first cover an unknown distance between the catheter and the vessel wall.

Once the needle tip 22 has been advanced to the desired tissue depth "D", the selected agent is injected into the periarterial space by known pressure injection means through the hypotube 20. In one embodiment, the agent is prepared by combining it with a viscous medium to prevent the agent from dissipating too rapidly within the tissues of the patient. In yet a further aspect, the agent may be delivered in particulate form through nano-particles or other micro-particles.

In some embodiments, use of the system may include the following additional steps. Once the agent has been injected into the perivascular space, the needle 20 may be withdrawn from its lumen 18 without removing the catheter 12 from the vasculature, and a fiber optic cable (not shown) may be advanced within the vacated lumen until the distal tip of the optic cable is positioned within the translucent portion 50 of the catheter. At this stage, light energy preferably in the form of laser energy may be directed into the proximal end of the optic cable, with the result that the light energy emerges from the distal tip of the cable, and passes through the translucent portion of the catheter into the vessel wall and thence into the tissue surrounding the vessel. By the process of photo activation, previously described above, the agent that has been injected into the periarterial space may be activated to provide its neurotoxic effect upon the renal nerve, and thereby providing a desired neuromodulating effect.

The catheter can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives. A variety of suitable configurations can be used including one or more of the tubular members formed of single or multiple layers or sections of tubing, as are conventionally known for catheter shaft design.

The term "catheter" should be understood to refer to a variety of device designs generally having an elongated structure configured for percutaneous advancement through a patient's vasculature. While the invention is described herein in terms of certain embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

The present invention may, of course, be carried out in other specific ways than those herein set forth without departing from the essential characteristics of the invention. The present embodiments are, therefore, to be considered in all respects as illustrative and not restrictive, while the scope of the invention is set forth in the claims that follow.

We claim:

1. A system for intravascular treatment, comprising:
    a catheter having an elongate axis defining a lumen configured for receiving a hypotube, the lumen terminating at a distal opening in an external side wall of the catheter;
    a hypotube slidably received within the lumen, the hypotube having a sharpened distal tip and being configured in relation to the catheter to have a retracted condition in which the distal tip is contained entirely within the lumen, and an advanced condition in which the distal tip protrudes from the distal opening;
    a plurality of positioning wires extending external to the catheter, the wires being configured in relation to the catheter to have an unexpanded condition for intravascular delivery in which each wire is collapsed against an external wall of the catheter, and an expanded condition for positioning the catheter within a vessel in which each wire is flexed away from the catheter along an imaginary plane extending radially away from the elongate axis, wherein all imaginary radial planes occupied by a flexed wire are included within an angular arc about the elongate axis of not more than 180 degrees; and further
    a pull element slidably received within a lumen of the catheter, wherein a distal end of each positioning wire is connected to the pull element whereby proximal movement of the pull element causes the positioning wires to flex and assume the expanded condition, wherein the pull element defines a lumen for receiving a guidewire;
    wherein the flexed wires in the expanded condition are located in relation to the catheter so that the angular arc has a center that is diametrically opposite the position of the distal opening.

2. The system of claim 1, further including a means for placing each positioning wire under a compressive axial force, whereby each wire is flexed away from the catheter in the expanded condition.

3. The system of claim 2, wherein the means for placing each positioning wire under a compressive axial force includes a pull element to which a distal end of each wire is attached, the pull element being configured for proximal movement in relation the catheter.

4. The system of claim 1, further including a means for moving the hypotube from the retracted condition distally to the advanced condition.

5. The system of claim 4, wherein the means for moving the hypotube from the retracted condition distally to the advanced condition includes a rack and pinion.

6. The system of claim 1, wherein the plurality of positioning wires are four in number.

7. The system of claim 1, further including a plurality of positioning lumens extending through the catheter, wherein each wire extends through a positioning lumen for at least a portion of the length of the wire.

8. The system of claim 1, wherein all imaginary radial planes occupied by a positioning wire are included within an angular arc about the elongate axis of not more than 120 degrees.

9. The system of claim 1, wherein the wires extend external to the catheter for a first length, and the distal opening is located at a position that is substantially midway along the first length.

* * * * *